(12) United States Patent
Suter

(10) Patent No.: US 7,963,565 B2
(45) Date of Patent: Jun. 21, 2011

(54) SYSTEM WITH ADAPTER FOR CLEANING MEDICAL APPLIANCES

(75) Inventor: Ursula Suter, Fehraltdorf (CH)

(73) Assignee: Oro CLean Chemie AG, Fehraltorf (CH)

( * ) Notice: Subject to any disclaimer, the term of this patent is extended or adjusted under 35 U.S.C. 154(b) by 618 days.

(21) Appl. No.: 12/068,092

(22) Filed: Feb. 1, 2008

(65) Prior Publication Data

US 2008/0199356 A1    Aug. 21, 2008

(30) Foreign Application Priority Data

Feb. 5, 2007   (EP) .................................... 07405031

(51) Int. Cl.
*F16L 35/00* (2006.01)
(52) U.S. Cl. .................. 285/4; 285/3; 285/13; 285/921; 604/110; 604/905
(58) Field of Classification Search .................. 285/3, 4, 285/14, 305, 921, 319, 13; 604/905, 110, 604/228
See application file for complete search history.

(56) References Cited

U.S. PATENT DOCUMENTS

| 4,367,738 | A | * | 1/1983 | Legendre et al. | 604/110 |
| 5,057,283 | A | | 10/1991 | Guggenheim et al. | |
| 5,197,953 | A | * | 3/1993 | Colonna | 604/110 |
| 5,458,576 | A | * | 10/1995 | Haber et al. | 604/110 |
| 5,489,272 | A | * | 2/1996 | Wirtz | 604/110 |
| 5,556,384 | A | * | 9/1996 | da Encarnac ao | 604/110 |
| 5,624,401 | A | * | 4/1997 | Leijd | 604/110 |
| 5,658,257 | A | * | 8/1997 | Ryles | 604/110 |
| 6,217,550 | B1 | * | 4/2001 | Capes | 604/110 |
| 6,875,205 | B2 | * | 4/2005 | Leinsing | 604/905 |

FOREIGN PATENT DOCUMENTS

| DE | 3239549 A1 | 4/1984 |
| EP | 0 709 056 A1 | 5/1996 |

* cited by examiner

*Primary Examiner* — David E Bochna
(74) *Attorney, Agent, or Firm* — Birch, Stewart, Kolasch & Birch, LLP

(57) ABSTRACT

An adapter (1) for cleaning a medical appliance comprises a fluid channel (2) with an inlet (3) and at least one outlet (4.1), at least one outlet being provided with a coupling unit (5.1) for an opening of a medical device. The coupling unit (5.1) is designed as a single-use coupling which, after the medical device has been coupled for the first time, generates a leak in the fluid channel at the time of uncoupling. This ensures totally hygienic cleaning of medical devices.

28 Claims, 3 Drawing Sheets

SYSTEM WITH ADAPTER FOR CLEANING MEDICAL APPLIANCES

BACKGROUND OF THE INVENTION

1. Field of the Invention

The invention relates to an adapter for treatment of a medical appliance, preferably a dental rotary instrument, comprising a fluid channel with an inlet and at least one outlet, at least one outlet being provided with a coupling means for an opening of a medical device. The invention also includes a set of equipment composed of an adapter and of a fluid container. The invention further relates to a method for treatment of the medical device using the adapter and the set of equipment.

2. Description of the Related Art

Medical devices that are contaminated by cells, blood, proteins, bacteria, physiological liquids or the like during use have to be thoroughly decontaminated and disinfected after each application. Only in this way can modern hygiene standards in the medical sector be guaranteed.

Dentistry in particular is affected by these demands. Rotary instruments (handpieces or angle pieces) for drills and similar tools have to be cleaned and disinfected or treated after each use on the patient. For this purpose, appliances already exist that carry out this work fully automatically. The fully automatic procedure guarantees complete cleaning and disinfection of the inside and outside of the rotary instruments and reduces the risk of germs being transferred from patient to patient. However, because of their cost, such appliances are as yet used only to a limited extent in industrialized nations.

Simpler mechanical versions exist as an alternative and are far less expensive. These are, for example, special adapters through which decontaminating or disinfecting sprays can be connected directly to the rotary instruments to be treated, in order to clean them on the inside. However, such devices require the involvement of a specialist, who carries out the cleaning procedure with great care in accordance with more or less elaborate instructions.

The disadvantage of using such adapters is that they too can become contaminated when coupled to the rotary instruments and, consequently, also have to be cleaned and disinfected. This represents an additional and risky step in the overall cleaning and disinfecting method.

SUMMARY OF THE INVENTION

The object of the invention is to create an adapter for medical devices which belongs to the technical field mentioned in the introduction and which is easy to use and ensures totally hygienic treatment of the medical devices.

According to one aspect of the invention, the adapter comprises a coupling means designed as a single-use coupling which, when removed for the first time from the medical device (after the first coupling), generates a leak in the fluid channel of the adapter, making it impossible to reuse the latter.

The present invention affords a number of advantages over the prior art. Thus, the single-use coupling ensures that an adapter can be used only once for treatment of a medical device, for example a rotary instrument. This avoids the need for careful cleaning and disinfecting of the adapter after use, thereby reducing the risk of cross-infections. At the same time, a hygienic mode of use of the adapter is ensured, since new, clean adapters have to be used for treatment of soiled medical appliances. If an adapter is fitted for example for a second time onto a medical device, for example a dental rotary instrument, the cleaning liquid flows out through the leak in the adapter. The compact structure of the adapter additionally permits inexpensive production.

The coupling means for medical devices is advantageously designed in the form of one or more snap-fit connections. These can be designed, for example, as structurally deformable protrusions on the adapter. Particularly suitable materials for the protrusions are plastics. If the opening of the medical device has an automatic locking mechanism, a mechanically stiff protrusion can also be mounted on the adapter in another variant. In both cases, the effect is that a mechanically stable and tight connection is obtained between the adapter and the medical device by simply pushing the two parts together.

The snap-fit connections are preferably designed as wedge-shaped locking lugs that protrude from the fluid channel preferably at an angle different than 90° and are particularly preferably inclined in the direction of the inlet of the adapter. This has the effect that the locking lugs can hook themselves into lateral recesses in the opening of the medical device. This locking mechanism provides a mechanically stable and fluid-tight connection between the adapter and the instrument opening, which connection can be undone again only by irreversibly damaging the adapter.

The snap-fit connections are particularly preferably mounted in areas of the fluid channel that have a reduced wall thickness and that are provided as predetermined break points. When the adapter is uncoupled from the medical opening, the snap-fit connection becomes hooked in the instrument and is buckled because of its inclination, and, when the load limit of the material of the fluid channel is reached, this leads to formation of a leak, for example in the form of a break or tear, at the predetermined break point of the fluid channel.

Sealing lips corresponding to the shape of the opening of the medical device are preferably mounted on the adapter. This permits a fluid-tight connection between the adapter and the medical device. Such sealing lips can be circular, oval, rectangular or of any other suitable shape that permits fluid-tight closure of the opening of the medical device. Arranging the sealing lips directly on the adapter has the advantage that the desired sealing of the connection is obtained automatically when the adapter is fitted onto the medical device.

Since many of the medical devices in widespread use today, in particular dental handpieces and angle pieces, have several internal fluid channels, for example liquid channels or air channels, it is particularly advantageous to use adapters with two or more outlets. The different outlets permit simultaneous cleaning of the different cavities (spray channels and gear channel), which simplifies and shortens the whole cleaning procedure. Because of the structure of rotary instruments, adapters of particular advantage are ones in which at least one outlet is oriented transversely with respect to a longitudinal direction of the fluid channel and at least one outlet is oriented along the longitudinal direction of the fluid channel. However, it is also possible to use other adapters with several channels that extend exclusively transversely or along the longitudinal direction of the adapter.

If an adapter has several outlets, the cross-sectional surface areas of the individual outlet openings in one advantageous variant are designed according to the geometry of the instrument and are also particularly advantageously of different sizes. The ratio of a cross-sectional surface area of a longitudinally oriented outlet opening to a cross-sectional surface area of a transversely oriented outlet opening preferably has a value in the range of 30-140. This has the effect that different amounts of fluid flow out of the different outlets. The targeted fluid distribution permitted by this means has the important advantage that the cleaning action in the different cavities of the medical device can be adapted to the degree of contamination and optimized.

Between the outlets, the adapter can also be provided with protrusions or lips that divide the opening of the medical device into parts separated from each other in a fluid-tight manner. These protrusions or lips are preferably adapted to the respective cross-sectional geometry of the opening of the medical device at the position of the protrusions or lips. Circular openings are of particular interest, since these are ideally suited for drills. The fluid-tight separation of the individual outlets means that the fluids used for cleaning can be distributed in a targeted manner to different areas of the medical devices and, if necessary, certain areas of the instruments can be protected from fluid.

Moreover, constrictions for regulating the stream of fluid through the adapter can be mounted in the fluid channel. These can have round, oval or rectangular cross sections and can be of different length. This has the effect that if the stream of fluid is too strong in the inlet area of the adapter, it can be substantially reduced in the area of the outlet openings, and in this way the coupling device of the adapter is protected against being overloaded by too great a pressure.

Moreover, a connecting device can be mounted in the area of the inlet of the adapter. In principle, all devices known from connecting techniques can be used. Threads, components for bayonet catches, components for Luer locks, clips or projections are preferably mounted. This has the advantage that the inlet side of the adapter can be connected to a wide variety of fluid containers, for example syringes, aerosol cans or fluid-carrying conduits.

The entire adapter is preferably made of only one material. Particularly suitable for this purpose are plastics, for example polypropylene, or similar materials. This means that the production costs can be kept down, while at the same time satisfying the requirement of chemical stability of the adapter.

Lateral holding projections for pulling and pushing are mounted on the adapter, making it easier to join and separate the adapter and the medical device. The holding projections protrude from the adapter preferably transverse to the longitudinal direction of the fluid channel and can be rectangular, elliptical, trapezoid or of any other suitable shape for transmitting sufficient pushing or pulling force to the adapter during coupling or uncoupling of the adapter by hand. The height of the holding projections from the adapter is advantageously more than 4 mm, to prevent the fingers slipping off during pulling and pushing.

For treatment, a fluid, for example a liquid cleaning or disinfecting agent, is conveyed through the adapter via the inlet of the adapter and into the cavities of the attached medical device that are to be cleaned and disinfected.

For this purpose, the inlet of the adapter is fitted with a fluid container, which advantageously includes a device for building up pressure in the fluid container. By means of the device for building up pressure, the fluid held in the container can easily be emptied into the adapter. In practice, syringes or aerosol cans have proven especially ideal, since their size means they are easy to handle. Aerosol cans additionally afford the advantage that, apart from being easy to handle, the continuous dispensing of fluid at constant pressure permits precise dosing of the cleaning agents. However, it is also possible to use larger fluid containers such as storage bottles or canisters which, for example, can also be connected to the adapter via a fluid conduit. In these cases, pumps that can be integrated into the fluid containers or conduits are particularly suitable for the build-up of pressure.

The use of the adapter according to the invention is of particular interest in connection with the treatment of dental handpieces and angle pieces. By virtue of the small dimensions of the adapter with the attached instrument and the syringe as fluid container, the entire set of equipment can be comfortably handled by a single person.

Individual treatment operations are preferably repeated several times with different fluids. In this way, medical devices can be freed of a wide variety of contaminants, for example blood, proteins, human cells or microorganisms. A typical treatment operation is as follows:

1. A syringe as liquid container is provided with a cleaning solution.
2. The adapter piece is coupled to the medical device, for example a rotary instrument.
3. The syringe is fitted on the inlet of the adapter.
4. The plunger of the syringe is pressed into the syringe, resulting in the build-up of an overpressure which causes the cleaning solution to flow through the adapter and through the cavities of the medical device that are to be cleaned.
5. The syringe is removed from the adapter and filled with air.
6. The air-filled syringe is again fitted onto the adapter and emptied, as a result of which remnants of the cleaning solution are ejected from the adapter and the medical device.
7. Steps 2-6 are preferably repeated using disinfecting solutions or other solutions.
8. The adapter piece is removed from the medical device and breaks open, as a result of which it becomes unusable.

Further advantageous configurations and combinations of features of the invention will become clear from the following detailed description and from the entirety of the patent claims.

BRIEF DESCRIPTION OF THE DRAWINGS

The illustrative embodiment is explained with reference to the drawings, in which.

In the figures, identical parts are in principle provided with identical reference signs.

DETAILED DESCRIPTION OF THE INVENTION

Figure 1:
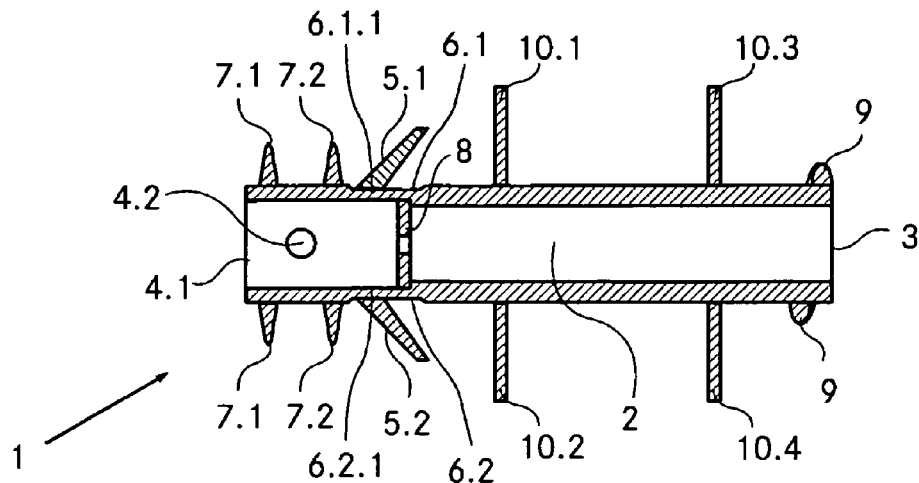
FIG. 1 shows a cross section through an adapter according to the invention.
Figure 2:
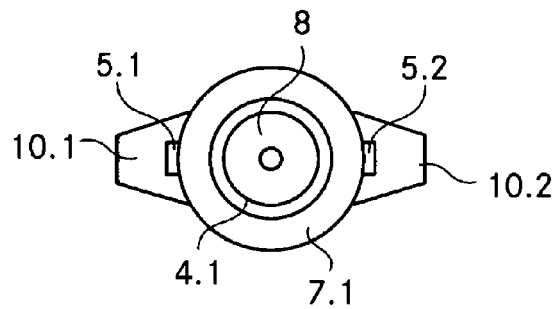
FIG. 2 shows a view of the outlet area of the adapter from FIG. 1, along the fluid channel.

An adapter 1 for a medical device, as shown in FIGS. 1 and 2, comprises a cylindrical fluid channel 2 with an inlet 3, a first outlet 4.1 along the direction of the fluid channel, and a second outlet 4.2 transverse thereto. The entire adapter 1 is made of polypropylene. In the area of the outlets 4.1, 4.2, the outside of the fluid channel 2 has two rectangular flattened portions 6.1, 6.2 on the outside of the cylindrical fluid channel 2, each of these carrying a coupling device in the form of two locking lugs 5.1, 5.2 for a snap-fit connection. Because of the flattened portions 6.1, 6.2, the wall thickness 6.1.1, 6.2.1 of the fluid channel 2 at the attachment surface of the locking lugs is smaller than in the other areas of the fluid channel 2. The locking lugs 5.1, 5.2 are wedge-shaped, are connected with their broad end to the flattened portions 6.1, 6.2, are inclined in the direction of the outlet 3, and protrude from the outside of the fluid channel at an angle of 50°, for example. Two sealing lips 7.1, 7.2 designed as annular flanges are mounted on the outside of the fluid channel 2 upstream and downstream of the transverse outlet 4.2. They completely enclose the adapter 1 on the outside and are designed as rings. The thickness of the sealing lips 7.1, 7.2 in cross section is at its greatest directly on the outside of the fluid channel 2 and decreases constantly in the direction away from the fluid channel. The external diameter of the sealing lips 7.1, 7.2 is chosen such that the radial heights of the sealing lips are smaller than the heights of the locking lugs 5.1, 5.2.

Arranged in the interior of the fluid channel 2 there is an annular constriction 8 that divides the fluid channel 2 into a front part toward the outlet area and a rear part toward the inlet area. The two parts have different diameters. A connecting device 9 in the form of a thread is mounted in the area of the inlet 3. In the area between inlet 3 and locking lugs 5.1, 5.2, the outside of the fluid channel 2 is provided with several holding projections 10.1, 10.2, 10.3, 10.4, which are perpendicular to the fluid channel 2 and have a trapezoid surface.

For commercially available dental rotary instruments, the sealing lips 7.1, 7.2 have an external diameter of 10 mm, for example, while the internal diameter of the longitudinally oriented outlet 4.1 is 5.8 mm, for example, and that of the transversely oriented outlet 4.2 is 0.5-1 mm, for example. The length of the entire adapter 1 is 48 mm, for example, and the holding projections 10.1, 10.2, 10.3, 10.4 protrude from the outside of the fluid channel 2 by preferably at least 4 mm.

Figure 3:
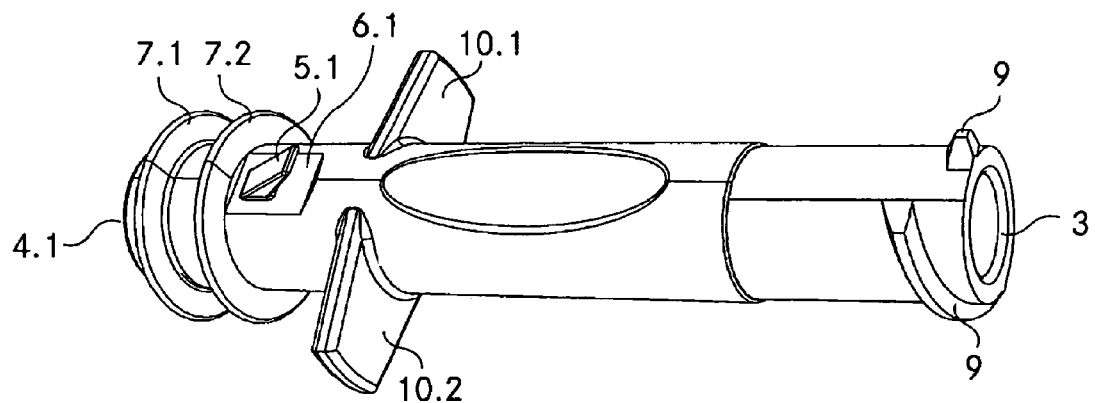
FIG. 3 shows a three-dimensional representation of a variant of the adapter from FIG. 1.

FIG. 3 shows an illustrative embodiment of an adapter 1 with only two holding projections 10.1, 10.2, which lie axially opposite each other and are also mounted perpendicular to the direction of the locking lugs 5.1, 5.2. Moreover, the outside of the fluid channel has an uneven design, which is helpful for handling the adapter 1.

Figures 4, 5:
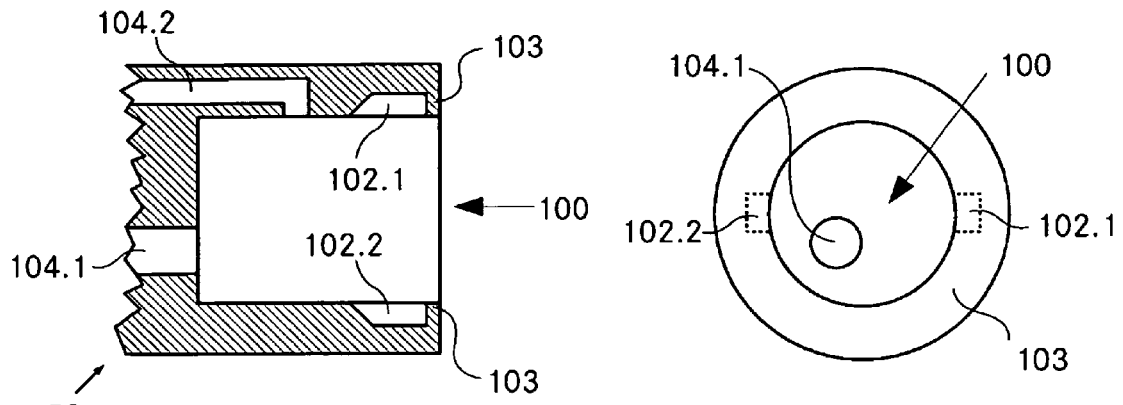
FIG. 4 shows a cross section through the opening of a dental rotary instrument.
FIG. 5 shows a view into the opening of a dental rotary instrument from FIG. 4.

The opening 100 of the medical device 50 can, for example, be a coupling piece of a rotary instrument for operating drills and similar rotary tools. Such instruments comprise, for example, a gear channel and spray channel, which become contaminated by cells, blood, proteins, microorganisms and physiological liquids during use. FIGS. 4 and 5 show an example of an opening 100 of a dental rotary instrument. It consists of a bore with a diameter corresponding to the radial diameter of the sealing lips 7.1, 7.2 of the adapter 1. Moreover, two depressions 102.1, 102.2 are present at the start of the bore and, because of their size, are able to receive the locking lugs 5.1, 5.2 in a state free from bending.

Figure 6:
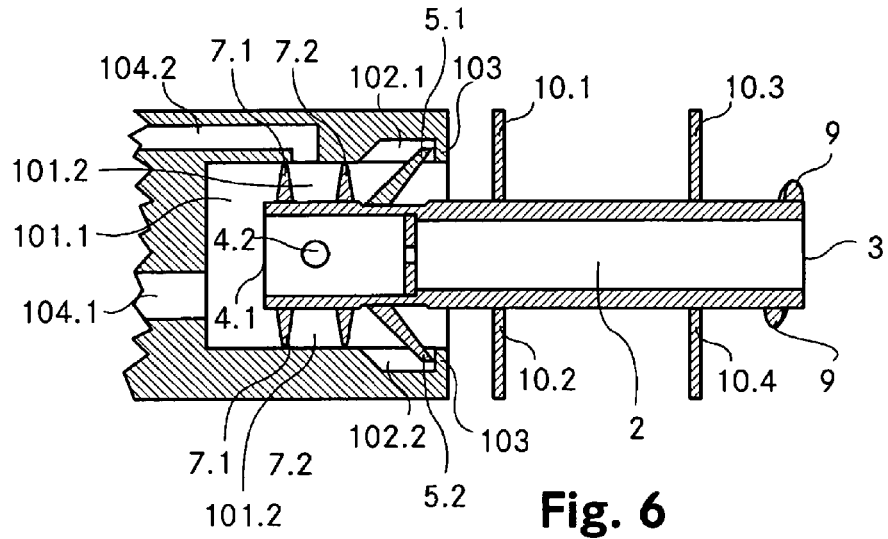
FIG. 6 shows an adapter coupled to a dental rotary instrument.

While the adapter 1 is being pushed into the opening 100 of the rotary instrument 50, using the holding projections 10.1, 10.2, 10.3, 10.4, the locking lugs 5.1, 5.2 are elastically compressed on the end face 103 of the bore and, after complete insertion, they deploy in the area of the depressions 102.1, 102.2 and lie there in a state free from bending. In this way, the adapter 1 snaps into place in the opening 100 of the medical device 50, as shown in FIG. 6, and a mechanically stable connection is obtained as a result of the depressions 102.1, 102.2 delimited by the end face 103. The sealing lips 7.1, 7.2 divide the bore into a first subsidiary volume 101.1, which communicates with a first fluid channel 104.1 of the rotary instrument, and a second subsidiary volume 101.2, which communicates with a second fluid channel 104.2 of the rotary instrument. The fluid channels 104.1, 104.2 lead from the opening 100 into other areas (not shown) of the rotary instrument 50.

Figure 7:
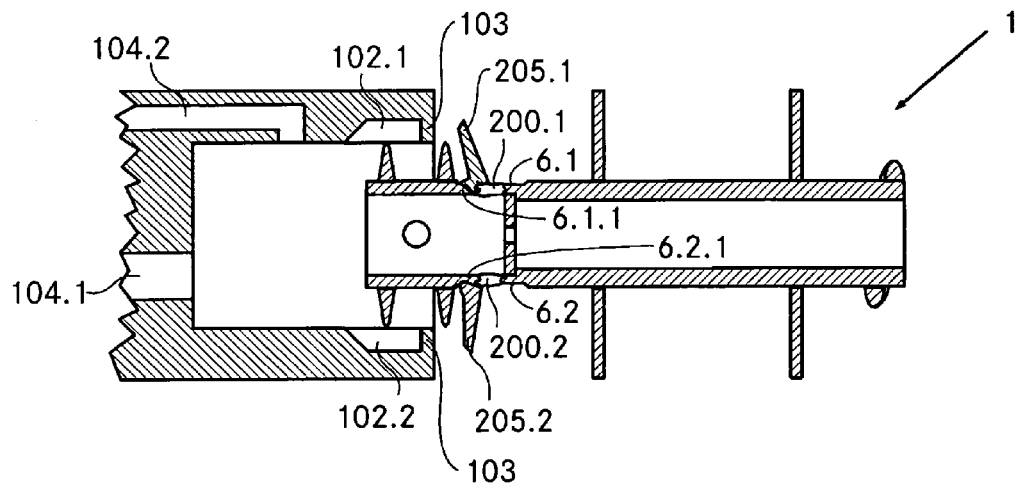
FIG. 7 shows an adapter after it has been uncoupled from the dental rotary instrument.

FIG. 7 shows the withdrawal or uncoupling of the adapter 1 from the opening 100 of the rotary instrument 50. The locking lugs catch against the end face 103 of the bore, as a result of which, in the area of the flattened portions 6.1, 6.2, and on account of the inclination of the locking lugs 5.1, 5.2, a lateral pressure is applied to the wall of the fluid channel, and, when the load limit of the material is reached, this pressure leads to the fluid channel 2 breaking. On account of the reduced wall thicknesses 6.1.1, 6.2.1 in the area of the flattened portions 6.1, 6.2, this leads to the irreversible formation of two leakage openings 200.1, 200.2 in the fluid channel 2, with the locking lugs 205.1, 205.2 being buckled in the opposite direction.

Figure 8:
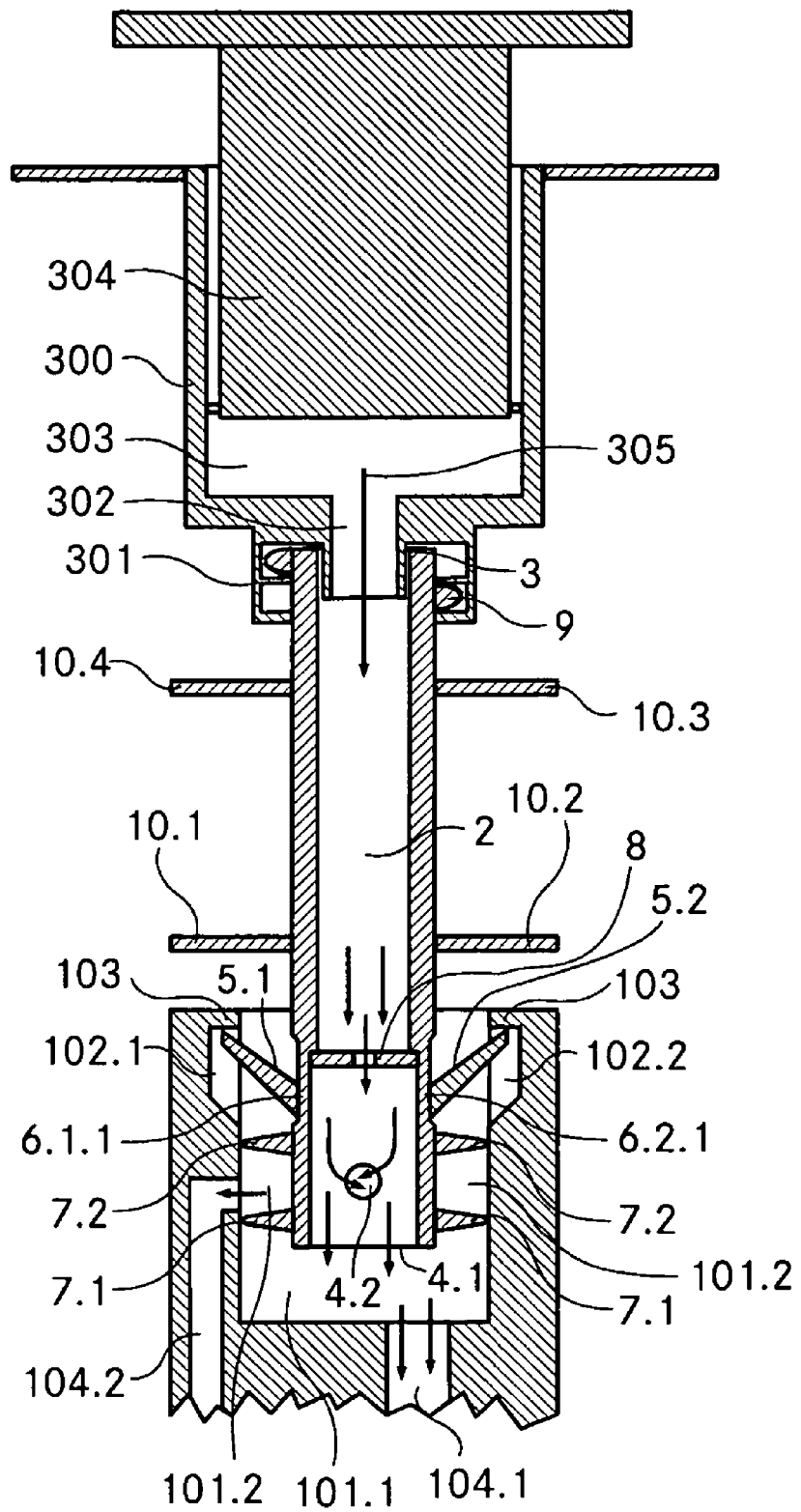
FIG. 8 shows an adapter coupled to a dental rotary instrument and to a fluid container.

To clean a rotary instrument 50, the outlet area of the adapter 1 is pushed into the opening 100 of the rotary instrument 50, and a fluid reservoir with a cleaning agent is fitted onto the inlet 3 of the adapter 1. In the illustrative embodiment shown in FIG. 8, a syringe 300 with an inner thread 301 is screwed onto the outer thread 9 of the adapter 1, as a result of which the syringe 300 is connected to the adapter 1 with a force fit and in a fluid-tight manner. The syringe outlet 302 opens directly into the fluid channel 2. In the fluid volume 303 of the syringe 300 there is a suitable fluid 305, for example a cleaning or disinfecting agent particularly in liquid form. By means of pressure on the syringe plunger 304, the fluid 305 is pressed into the fluid channel 2 and, after the stream of fluid is throttled by the constriction 8, arrives at the outlets 4.1, 4.2 of the adapter 1. To ensure a fluid-tight connection between the adapter 1 and the opening 100 of the rotary instrument 50, the locking lugs 5.1, 5.2 have to be locked in the depressions 102.1, 102.2. Otherwise, the adapter 1 is pushed back out of the opening 100 of the instrument 50 by the fluid pressure. Because of the different geometries and different sizes of the cross-sectional surface areas of the outlets 4.1, 4.2, streams of fluid flow at different strengths into the subsidiary volumes 101.1, 101.2 and from there onward into the cavities 104.1, 104.2 of the opening 100 of the instrument 50. In this way, the fluid channels 104.1, 104.2, and further inward areas (not shown) of the instrument 50, are cleaned by the fluid 305. The targeted control of the strength of the streams of fluid through the differently dimensioned outlets 4.1, 4.2 is particularly advantageous if, for example, the second channel 104.2 of the rotary instrument is only lightly contaminated compared to the first channel 104.1. By virtue of the smaller cross-sectional surface area and geometric arrangement of the second outlet 4.2 compared to the first outlet 4.1, a smaller amount of cleaning agent flows through the channel 104.2, which considerably reduces the consumption.

To clean dental rotary instruments for example, several cleaning steps are preferably carried out one after another. First, the adapter 1 is coupled into the opening 100 of the instrument, such that the locking lugs 5.1, 5.2 lock in the depressions 102.1, 102.2. A syringe 300, provided with a cleaning solution, is then screwed onto the inlet 3 of the adapter. Thereafter, when pressure is applied to the plunger 304 of the syringe, the cleaning agent is conveyed into the fluid channel 2 of the adapter 1 and, as has been described above, is conveyed onward through the instrument's fluid channels 104.1, 104.2 that are to be cleaned. The syringe 300 with the cleaning agent is thereafter unscrewed from the inlet 2 of the adapter 1, and the syringe 300, filled with air, is screwed onto the inlet 2 of the adapter 1. Analogously to the cleaning agent, the air is also conveyed through the fluid channels 104.1, 104.2 of the dental instrument. The residues of the cleaning agent from the preceding cleaning step are thereby removed from the opening 100 and from the fluid channels 104.1, 104.2 of the instrument. Thereafter, the syringe 300 is removed from the inlet 2 of the adapter 1 and, provided with a disinfecting agent, is screwed back onto the inlet 2 of the adapter 1. Analogously to the cleaning agent, the disinfecting agent too is conveyed through the fluid channels 104.1, 104.2 of the dental handpiece, and the syringe 300 is then removed. Then, using the syringe, air is then conveyed analogously through the opening 100 and the fluid channels 104.1, 104.2 of the rotary instrument, and residues of the disinfecting agent are blown out. When cleaning is completed, the adapter 1 is withdrawn from the opening of the medical device, whereupon the adapter breaks open, as has been described above and shown in FIG. 7, and is rendered unusable.

The following example demonstrates the efficiency of cleaning a medical device in the form of a contra angle handpiece using the adapter 1. For this example, a contra angle handpiece was artificially contaminated with a suspension of test organisms that are commonly used to test the activity of chemical disinfectant. These test organisms were *Mycobacterium terrae* (ATCC 15755), *Staphylococcus aureus* (ATCC 6538), *Enterococcus hirae* (ATCC 10541), *Escherichia coli* K12 (NCTC 10538), *Pseudomonas aeruginosa* (ATCC 15442), *Candida albicans* (ATCC 10231). For each test organism, the following procedure comprising steps A-C was carried out:

Step A: Contamination of the Contra Angle

Thoroughly clean and sterile contra angle handpieces from Kavo was contaminated inside with 3×100 µl of the test suspension, the respective cell concentration of which is stated in Table 5 as CFU (colony forming units) per ml. Subsequently, the outer surface of the contra angle was contaminated with 3×100 µl of the respective test suspension. The contra angle was then left to dry on a sterile paper.

Step B: Cleaning and Disinfection of the Contra Angle Handpiece with the Help of the Adapter 1

The cleaning and disinfection procedure using the system with adapter 1 was performed according to the sequence shown in Table 1:

TABLE 1

| Step | Procedure |
|---|---|
| B.1 | The outer surface of the contra angle handpiece was sprayed with a disinfecting solution as speciefied in Table 2 and the disinfecting solution was acting on the the outer surface for 30 sec. |
| B.2 | The adapter 1 was attached on the contra angle handpiece and a syringe was screwed on to the inlet 3 of the adapter 1, whereby the syringe was filled with 10 ml of cleaning solution as specified in Table 3. |
| B.3 | 5 ml of the cleaning solution was pushed through the contra-angle handpiece. After 1 minute of waiting, the residual cleaning solution in the syringe was pushed through the contra-angle handpiece. |
| B.4 | The residual cleaning solution was removed from the contra angle handpiece by blowing 10 ml air through it with the help of the syringe. |
| B.5 | A syringe filled with 10 ml of disinfection solution (Table 2) was screwed to the adapter 1. |
| B.6 | 5 ml of the disinfection solution was pushed through the contra-angle handpiece. After 1 minute of waiting, the residual disinfection solution in the syringe was pushed through the contra-angle handpiece. |
| B.7 | The residual disinfection solution was removed from the contra angle handpiece by blowing 10 ml of air through it with the help of the syringe. |
| B.8 | The adapter 1 was withdrawn from the contra angle handpiece, whereupon the adapter 1 broke open. |
| B.9 | The outer surface of the contra angle handpiece was sprayed with the disinfecting solution as specified in Table 2. After acting for 30 sec the disinfecting solution was wiped off with a cotton swab. |

TABLE 2

Disifection solution

| Ingredient | Amount |
|---|---|
| Ethanol | 20 g |
| 1-Propanol | 28 g |
| Quaternary ammonium compounds | 0.1 g |
| Perfumes | |

TABLE 3

Cleaning solution

| Ingredient | Amount |
|---|---|
| Alkyl amine | 0.7% |
| Anionic surfactants | 0.25% |
| Non-ionic surfactants | 0.25% |
| Perfumes, Dyes | |
| Water | Balance |

All steps B.1-B.9 were performed at 20-25° C.
For the positive control, steps B.1-B.9 were omitted.

Step C: Re-Extraction of the Residual Contamination Cells from the Contra Angle

A 50 ml tube was filled with 20 ml of the neutralization solution as specified in Table 4. The contra angle handpiece was placed in the tube; the tube was closed hermetically and shaken 50 times with strong vertical shakes. The resulting neutralization solution was diluted up to $10^{-6}$ and 2×0.5 ml from the undiluted solution and every dilution was plated on the Petri agar plates. The plates with bacteria were incubated for 48 h at 37° C. and plates with *Candida albicans* were incubated for 48 h at 30°. The ability of the neutralization solution to neutralize the cleaning and the disinfecting solution and the non-toxicity of the neutralization solution were tested for each test suspension in preliminary experiments.

Results are given in Table 5. The positive control shows the $\log_{10}$ CFU/ml of cells that survive the procedure of contamination and re-extraction (Steps A and C). The column residual cell shows the $\log_{10}$ CFU/ml of the cells that survive the procedure of contamination, cleaning/disinfection and re-extraction (Steps A, B and C). The difference between positive control and residual cells is taken as the $\log_{10}$ reduction factor and represents the disinfection activity of the procedure. It is known that the German Society for Hygiene and Microbiology requires that disinfectants for instrument achieve a reduction factor of at least 4 $\log^{10}$ (99.99%) for *Candida albicans* and *Mycobacterium terrae* and a reduction factor of at least 5

$\log_{10}$ (99.999%) for the other strains of the Table 5. European Norms regulating chemical disinfectants have similar requirements. Thus the method described here has much higher disinfection activity that is required from German Society for Hygiene and Microbiology or European Norms.

TABLE 4

Neutralization solution

| Ingredient | Amount |
| --- | --- |
| Tween 80 | 3.0% |
| Lecithine | 0.3% |
| Histidine | 0.1% |
| sodium thiosulfate in casein-soybean broth | 0.5% |
| Water | Balance |

TABLE 5

Results

| Strain | Test suspension CFU/ml | Positive control $\log_{10}$ CFU/ml | Residual cells $\log_{10}$ CFU/ml | $\log_{10}$ reduction |
| --- | --- | --- | --- | --- |
| Mycobacterium terrae (ATCC 15755) | $1.52 \times 10^9$ | 7.22 | 1.00 | 6.22 |
| Staphylococcus aureus (ATCC 6538) | $6.47 \times 10^9$ | 7.93 | 0.00 | 7.93 |
| Enterococcus hirae (ATCC 10541) | $3.00 \times 10^9$ | 7.86 | 0.00 | 7.86 |
| Escherichia coli K12 (NCTC 10538) | $2.26 \times 10^9$ | 7.28 | 0.00 | 7.28 |
| Pseudomonas aeruginosa (ATCC 15442) | $4.12 \times 10^9$ | 7.97 | 0.00 | 7.97 |
| Candida albicans (ATCC 10231) | $1.6 \times 10^9$ | 7.38 | 0.00 | 7.38 |

In other configurations, the adapter 1 can have a curved or angled fluid channel 2 and, for example, can also have the shape of an oval or rectangular hollow profile. In particular, additional protrusions or edges can be mounted on the adapter 1 for defined orientation relative to the medical device. The fluid channel 2 can have a constant internal diameter along its entire length or can have different areas with different internal diameters and several constrictions. The number of sealing lips 7.1, 7.2 and of connecting devices 5.1, 5.2 depends on the configuration of the medical device and can accordingly vary. In particular, more than two outlets 4.1, 4.2 can be provided and can extend in any desired direction relative to the longitudinal direction of the fluid channel 2. In particular, the areas of reduced wall thickness 6.1.1, 6.2.1 serving as predetermined break points in the fluid channel 2 can also be designed as an annular narrowing in the whole circumference of the fluid channel 2 or as slit-shaped indentations.

In the area of the inlet 3, it is possible to provide, instead of the thread 9, a component of a bayonet catch, a component of a Luer lock, a clip or a projection. The geometric shapes of the inlet and of the outlets can be different and can have asymmetries, corners, or flattened portions of the edges. Likewise, depending on the design of the adapter 1, the holding projections 10.1, 10.2, 10.3, 10.4 can be mounted at other locations and in different numbers on the adapter, in order to optimize handling when coupling and uncoupling the medical device 50.

Other configurations of the opening 100 of the medical device 50 are also possible. In particular, more than two fluid channels 104.1, 104.2 can lead from the opening into inner areas of the medical device. Other geometries, for example noncircular ones, are also possible, with asymmetrical recesses that ensure a defined orientation of the adapter 1 in terms of rotation about the axis of the opening 100 of the medical device 50. The adapter 1 is in these cases correspondingly adapted to the opening present in the medical device 50.

In another advantageous configuration, a tube can be coupled, instead of a syringe 300, to the inlet 3 of the adapter and connects the adapter 1 to a storage bottle or a canister via a pump. Pressurized aerosol cans in particular can also serve as the fluid reservoir and can be connected via a tube to the inlet 3 of the adapter 1. Likewise, instead of threads as the connecting devices 9, 301, it is also possible for other connecting elements, for example clips, projections or components of bayonet catches, to be mounted on the adapter 1 and on the fluid reservoir.

Depending on the medical device 50, it may be advantageous to use additional cleaning agents that dissolve specific contaminants. These can be present in particular as liquids, gases or aerosols. Instead of air, any other gaseous fluid, e.g. nitrogen or noble gases, can of course be used to blow the cleaning or disinfecting agents from the opening 100 and the fluid channels 104.1, 104.2 of the medical device.

In conclusion, a novel adapter for connecting a fluid reservoir to the opening of a medical device, e.g. a rotary instrument, has been developed, which ensures totally hygienic cleaning of instruments. The adapter is based on a connecting device which, when the adapter is uncoupled from the opening of the medical device, leads to the breaking of the adapter. Consequently, an adapter can always only be used to clean a single medical device. The adapters according to the invention can in principle be used for all medical devices that have openings in the housing.

The invention claimed is:

1. An adapter for treatment of a medical appliance, comprising:
    a fluid channel with an inlet and at least one outlet, at least one outlet being provided with coupling means for an opening of a medical device,
    wherein the coupling means is designed as a single-use coupling which, when removed for the first time from the medical device, generates a leak in the fluid channel of the adapter,
    wherein the coupling means for the opening of the medical device is designed as one or more snap-fit connections, and
    wherein the snap-fit connections are mounted in areas of the fluid channel that have a reduced wall thickness.

2. The adapter according to claim 1, wherein the snap-fit connections are structurally bendable.

3. The adapter according to claim 1, wherein the snap-fit connections are made of plastic.

4. The adapter according to claim 1, wherein the snap-fit connections are designed as wedge-shaped locking lugs.

5. The adapter according to claim 1, wherein the snap-fit connections protrude from the fluid channel at an angle different than 90°.

6. The adapter according to claim 5, wherein the snap-fit connections are inclined in the direction of the inlet.

7. The adapter according to claim 1, wherein sealing lips corresponding to the shape of the opening of the medical device are mounted on the adapter and permit a fluid-tight connection between the adapter and the medical device.

8. The adapter according to claim 1, wherein the adapter includes two or more outlets.

9. The adapter according to claim 8, wherein at least one outlet is oriented transversely with respect to a longitudinal direction of the fluid channel and at least one outlet is oriented along the longitudinal direction of the fluid channel.

10. The adapter according to claim 8 wherein the cross-sectional surface areas of the outlet openings are of different sizes.

11. The adapter according to claim 10, wherein a ratio of a cross-sectional surface area of a longitudinally oriented outlet opening to a cross-sectional surface area of a transversely oriented outlet opening has a value in the range of 30-140.

12. The adapter according to claim 8, wherein between the outlets, the adapter is provided with protrusions or lips that divide the opening of the medical device into parts separated from each other in a fluid-tight manner, and the protrusions or lips are adapted to the respective cross-sectional geometry of the opening of the medical device.

13. The adapter according to claim 1, wherein a constriction for throttling the stream of fluid through the adapter is mounted in the fluid channel.

14. The adapter according to claim 1, wherein a connecting device is mounted in an area of the inlet of the adapter.

15. The adapter according to claim 14, wherein the connecting device is a thread, a component of a bayonet catch, a component of a Luer lock, a clip, or a projection.

16. The adapter according to claim 1, wherein the entire adapter is made of only one material.

17. The adapter according to claim 16, wherein the material is plastic.

18. The adapter according to claim 17, wherein plastic is polypropylene.

19. The adapter according to claim 1, wherein lateral holding projections for pulling and pushing are mounted on the adapter, making it easier to join and separate the adapter and the medical device.

20. The adapter according to claim 19, wherein the height of the holding projections from the outside of the adapter is more than 4 mm.

21. A set of equipment, comprising:
a medical device;
an adapter according to claim 1; and
a fluid container,
wherein the inlet of the adapter is connected in a fluid-tight manner to the fluid container.

22. The set of equipment according to claim 21, wherein the fluid container comprises a device for pressure build-up.

23. The set of equipment according to claim 21, wherein the at least one of the adapter are coupled in a fluid-tight manner to the medical device.

24. The set of equipment according to claim 21, wherein the medical device is a dental rotary instrument.

25. An adapter for treatment of a medical appliance, comprising:
a fluid channel with an inlet and at least one outlet, at least one outlet being provided with coupling means for an opening of a medical device,
wherein the coupling means is designed as a single-use coupling which, when removed for the first time from the medical device, generates a leak in the fluid channel of the adapter,
wherein the coupling means for the opening of the medical device is designed as one or more snap-fit connections, and
wherein the snap-fit connections are designed as wedge-shaped locking lugs.

26. An adapter for treatment of a medical appliance, comprising:
a fluid channel with an inlet and at least one outlet, at least one outlet being provided with coupling means for an opening of a medical device,
wherein the coupling means is designed as a single-use coupling which, when removed for the first time from the medical device, generates a leak in the fluid channel of the adapter,
wherein the coupling means for the opening of the medical device is designed as one or more snap-fit connections, and
wherein the snap-fit connections protrude from the fluid channel at an angle different than 90°.

27. An adapter for treatment of a medical appliance, comprising:
a fluid channel with an inlet and at least one outlet, at least one outlet being provided with coupling means for an opening of a medical device,
wherein the coupling means is designed as a single-use coupling which, when removed for the first time from the medical device, generates a leak in the fluid channel of the adapter, and
wherein the adapter includes two or more outlets.

28. A set of equipment comprising:
a medical device;
an adapter including,
a fluid channel with an inlet and at least one outlet, at least one outlet being provided with coupling means for an opening of a medical device,
wherein the coupling means is designed as a single-use coupling which, when removed for the first time from the medical device, generates a leak in the fluid channel of the adapter; and
a fluid container,
wherein the inlet of the adapter is connected in a fluid-tight manner to the fluid container, and
wherein the medical device is a dental rotary instrument.

* * * * *